United States Patent
Farris

(10) Patent No.: US 6,547,099 B1
(45) Date of Patent: *Apr. 15, 2003

(54) MEDICINAL DOSING APPARATUS AND METHOD

(76) Inventor: Barry Farris, P.O. Box 1817, Zephyr Cove, NV (US) 89948

( * ) Notice: Subject to any disclaimer, the term of this patent is extended or adjusted under 35 U.S.C. 154(b) by 0 days.

This patent is subject to a terminal disclaimer.

(21) Appl. No.: 09/927,686

(22) Filed: Aug. 9, 2001

Related U.S. Application Data

(63) Continuation of application No. 09/258,085, filed on Feb. 25, 1999.

(51) Int. Cl.$^7$ ............................................. B65D 35/28
(52) U.S. Cl. ........................... 222/95; 222/97; 222/98; 222/102; 222/210
(58) Field of Search .................. 222/95, 97, 98, 222/102, 210

(56) References Cited

U.S. PATENT DOCUMENTS

| | | |
|---|---|---|
| 756,842 A | 4/1904 | Emmons |
| 829,178 A | 8/1906 | Stegmaier |
| 1,386,966 A | 8/1921 | Slade |
| 1,643,531 A | 9/1927 | Wolf |
| 1,762,430 A | 6/1930 | Tokita |
| 1,773,104 A | 8/1930 | Johnson |
| 2,197,958 A | 4/1940 | Waters |
| 2,486,321 A | 10/1949 | O'Sullivan |
| 2,667,165 A | 1/1954 | Smith |
| 2,667,872 A | 2/1954 | Smith |
| 2,744,527 A | 5/1956 | Barrett et al. |
| 2,744,528 A | 5/1956 | Barrett et al. |
| 2,748,770 A | 6/1956 | Moeck |
| 2,768,623 A | 10/1956 | Marchand |
| 2,881,953 A | 4/1959 | Kuschel |
| 2,911,972 A | 11/1959 | Elinger |
| 3,078,847 A | 2/1963 | Wandell et al. |
| 3,089,489 A | 5/1963 | Dunmire |
| 3,142,074 A | 7/1964 | Reich |
| 3,187,966 A | 6/1965 | Klygis |
| 3,194,452 A | 7/1965 | Sanderford |
| 3,198,385 A | 8/1965 | Maxwell |
| 3,261,381 A | 7/1966 | Roach |
| 3,335,914 A | 8/1967 | Starzdins et al. |
| 3,340,869 A | 9/1967 | Bane |
| 3,419,007 A | 12/1968 | Love |

(List continued on next page.)

FOREIGN PATENT DOCUMENTS

| | | |
|---|---|---|
| AU | 278032 | 12/1965 |
| CH | 279468 | 11/1951 |
| DE | 446819 | 1/1928 |
| DE | 556491 | 8/1932 |
| DE | 577611 | 6/1933 |
| DE | 3827 335 A | 2/1990 |
| EP | 0 324 257 | 7/1989 |
| EP | 0 350 772 | 7/1998 |
| FR | 470700 | 6/1914 |
| FR | 1316596 | 12/1962 |
| FR | 1330410 | 5/1963 |
| FR | 2058585 | 5/1971 |
| FR | 2594687 A | 8/1987 |
| GB | 386298 | 2/1933 |
| GB | 557400 | 11/1943 |
| NL | 92396 | 10/1959 |
| SU | 1553 135 A | 3/1990 |
| WO | WO 87/01944 | 4/1987 |

OTHER PUBLICATIONS

US 5,478,322, 12/1995, Farris et al. (withdrawn).

*Primary Examiner*—Gene Mancene
*Assistant Examiner*—Frederick C. Nicolas
(74) *Attorney, Agent, or Firm*—Bernhard Kreten

(57) ABSTRACT

External manipulation of a prefilled vial to dispense its contents by deforming the vial is disclosed.

7 Claims, 5 Drawing Sheets

U.S. PATENT DOCUMENTS

| | | |
|---|---|---|
| 3,557,788 A | 1/1971 | Swartz |
| 3,604,418 A | 9/1971 | Jones |
| 3,712,295 A | 1/1973 | Kline |
| 3,736,933 A | 6/1973 | Szabo |
| 3,938,514 A | 2/1976 | Boucher |
| 3,977,553 A | 8/1976 | Cornett, III et al. |
| 4,018,222 A | 4/1977 | McAleer et al. |
| 4,046,145 A | 9/1977 | Choksi et al. |
| D246,321 S | 11/1977 | Löfman |
| 4,130,117 A | 12/1978 | Van Eck |
| 4,168,032 A | 9/1979 | Sneider |
| 4,213,456 A | 7/1980 | Böttger |
| 4,248,227 A | 2/1981 | Thomas |
| 4,282,986 A | 8/1981 | af Ekenstam et al. |
| 4,357,937 A | 11/1982 | Burrell, Jr. et al. |
| 4,411,656 A | 10/1983 | Cornett, III |
| 4,465,472 A | 8/1984 | Urbaniak |
| 4,502,616 A | 3/1985 | Meierhoefer |
| 4,506,793 A | 3/1985 | MacGregor et al. |
| 4,548,601 A | 10/1985 | Lary |
| 4,610,670 A | 9/1986 | Spencer |
| 4,643,309 A | 2/1987 | Evers |
| 4,753,638 A | 6/1988 | Peters |
| 4,883,473 A | 11/1989 | Thomas |
| 4,944,736 A | 7/1990 | Holtz |
| 4,955,871 A | 9/1990 | Thomas |
| 4,966,312 A | 10/1990 | Waring |
| 4,994,039 A | 2/1991 | Mattson |
| 5,035,689 A | 7/1991 | Schroeder |
| 5,102,398 A | 4/1992 | Farris |
| 5,201,751 A | 4/1993 | Cohen |
| 5,215,221 A | 6/1993 | Dirksing |
| 5,222,948 A | 6/1993 | Austin et al. |
| 5,222,950 A | 6/1993 | Eisenberg |
| 5,242,422 A | 9/1993 | Schneberger et al. |
| 5,261,881 A | 11/1993 | Riner |
| 5,334,173 A | 8/1994 | Armstrong, Jr. |
| 5,356,406 A | 10/1994 | Schraga |
| 5,370,626 A | 12/1994 | Farris |
| 5,374,263 A | 12/1994 | Weiler |
| 5,409,125 A | 4/1995 | Kimber et al. |
| 5,509,906 A | 4/1996 | Poynter |
| 5,538,506 A | 7/1996 | Farris et al. |
| 5,657,903 A | 8/1997 | Roberts |
| 5,690,253 A | 11/1997 | LaFleur |
| 5,716,346 A | 2/1998 | Farris |
| 6,045,538 A | 4/2000 | Farris |

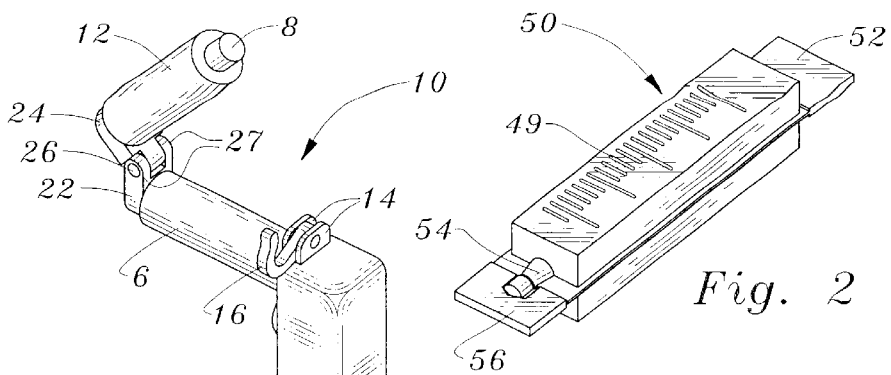
Fig. 1
Fig. 2
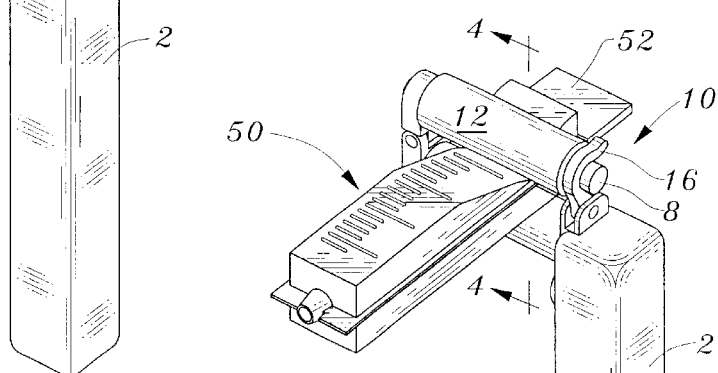
Fig. 3
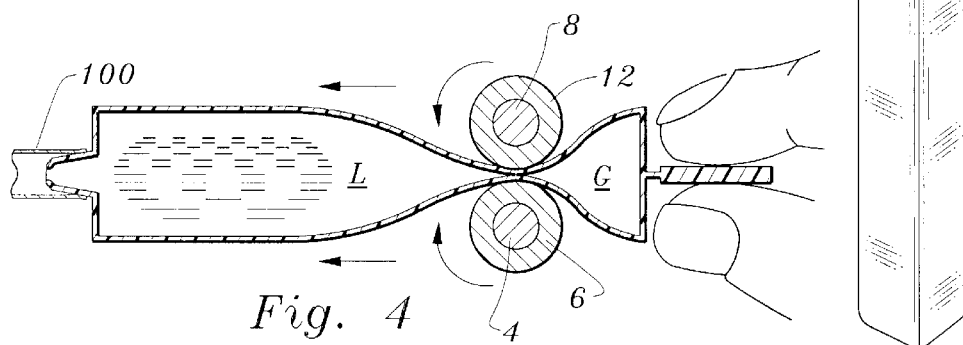
Fig. 4
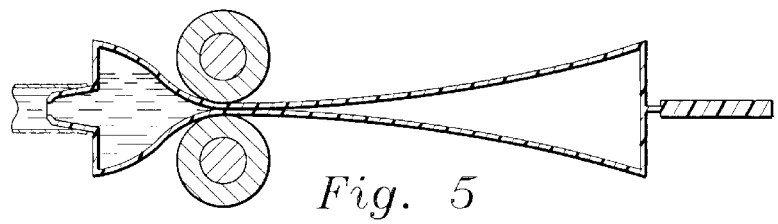
Fig. 5

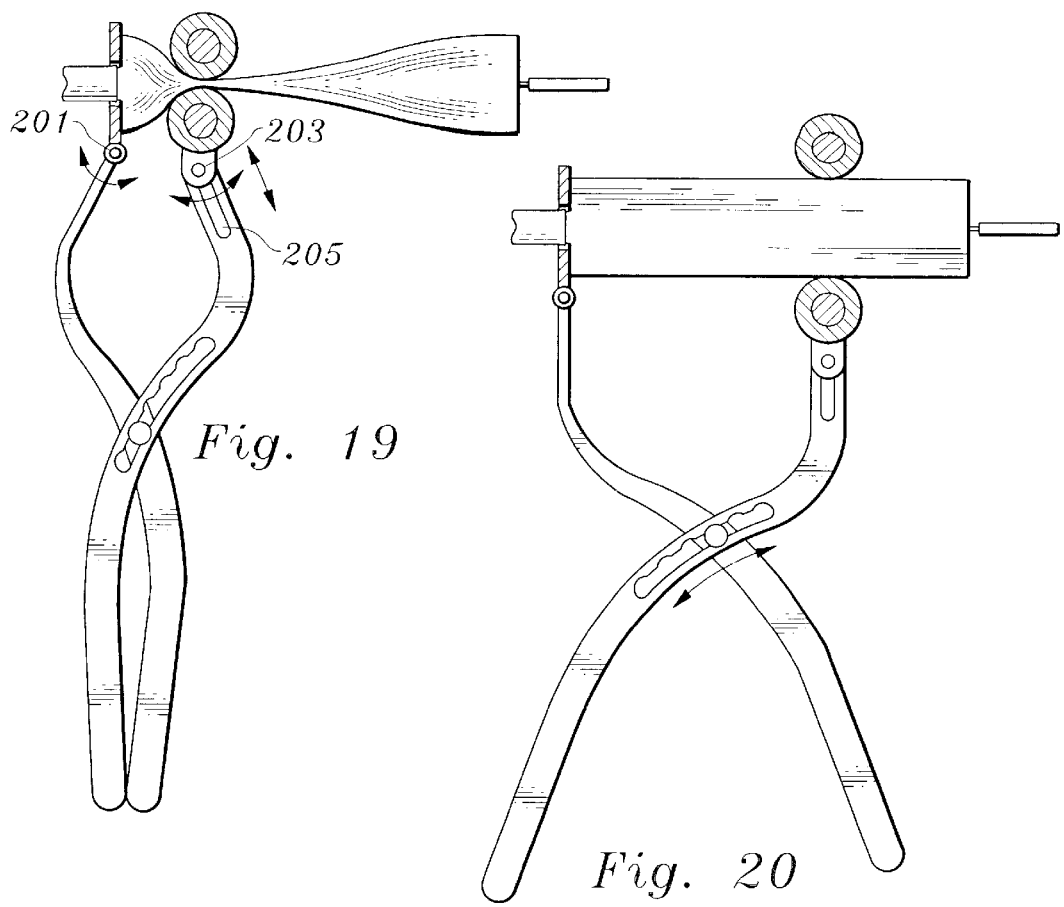
Fig. 19
Fig. 20
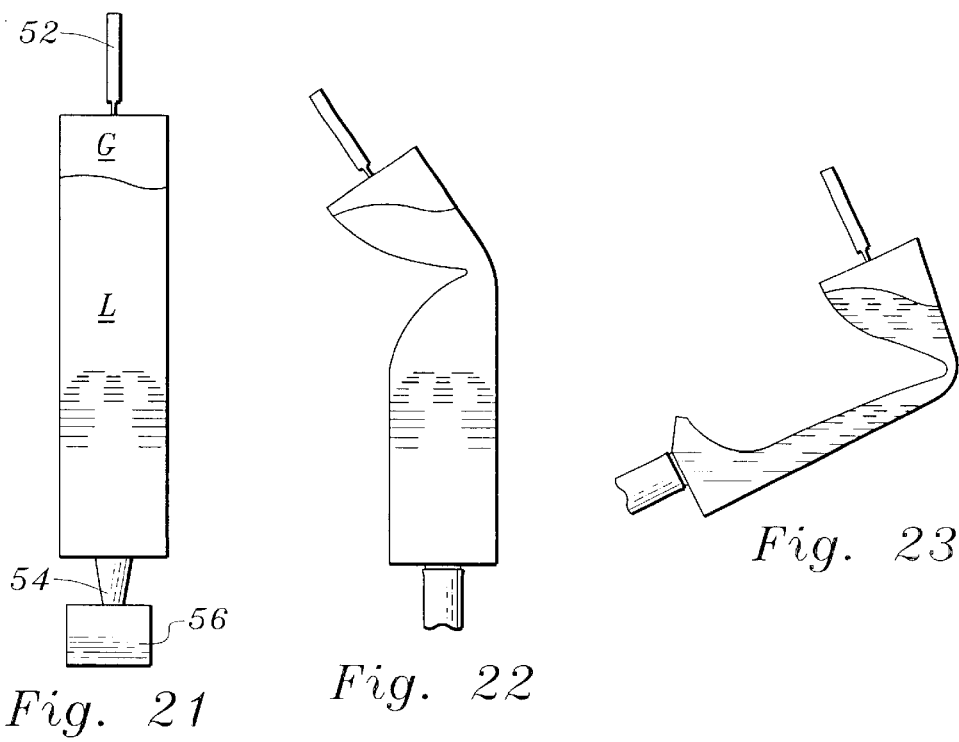
Fig. 21
Fig. 22
Fig. 23

MEDICINAL DOSING APPARATUS AND METHOD

This application is a continuation of U.S. application Ser. No. 09/258,085, filed Feb. 25, 1999, pending.

FIELD OF THE INVENTION

The following invention relates generally to instrumentalities for administering doses of medicaments. More particularly, the instant invention is directed to a vial formed from elastically deformable material which is externally manipulated in order to squeeze the contents of the vial out of the vial and thus be dispensed.

BACKGROUND OF THE INVENTION

Syringes are well known medicinal dosing devices. In essence, they operate by having a substantially cylindrical bore within which a piston reciprocates. One end of the cylindrical bore admits and dispels fluid from the interior while another end of the cylinder allows a piston plunger to be received for axial translation in providing the propelling force for the introduction and utilization of the liquid.

While these devices perform the avowed purpose of dispensing medicine, they have changed little since their inception. Typically, the piston includes a peripheral seal at an end thereof within the cylinder of the syringe and remote from the plunger. This seal is frequently lubricated with silicone to reduce the co-efficient of friction and may include latex, both ingredients of which have been the subject matter of ongoing scrutiny with respect to adverse patient reactions to these two products. In addition, in order for the syringe to receive the fluid, they either must be prefilled which provides an opportunity for contamination during the prefilling process, or they must be subsequently filled at the site of usage which requires that the syringe cooperate with an ampoule or a vial for fluid transferal.

In response to these problems, applicant has devised a series of prefilled syringes which are formed asepticly and are filled concurrently in a blow-fill seal process. These prefilled, blow-filled seal syringes have dispensed for the need of receiving fluid from another source after the manufacture of the syringe, since the syringe is filled concurrently at its site of fabrication. While this product operates quite efficient and admirably, applicant has developed other devices in order to provide solutions to problems in related areas of this industry.

For example, applicant has devised an ampoule which is elastically deformable and prefilled using blow-fill seal technology which can dock with existing, conventional, known syringes in order to provide a more economical ampoule or vial where preference still exists for a conventional syringe.

The following prior art reflects the state of the art of which applicant is aware and is included herewith to discharge applicant's avowed duty to disclose relevant prior art. It is respectfully submitted, however, that none of the prior art when considered singly or in any conceivable, permissible combination teaches or renders obvious the instant invention set forth hereinafter.

| PATENT NO. | ISSUE DATE | INVENTOR |
| --- | --- | --- |
| 829,178 | August 21, 1906 | Stegmaier |
| 1,643,531 | September 27, 1927 | Wolf |
| 1,762,430 | June 10, 1930 | Tokita |
| 2,486,321 | October 25, 1949 | O'Sullivan |

-continued

| | | |
| --- | --- | --- |
| 2,667,165 | January 26, 1954 | Smith |
| 2,667,872 | February 2, 1954 | Smith |
| 2,744,527 | May 8, 1956 | Barrett, et al. |
| 2,744,528 | May 8, 1956 | Barrett, et al. |
| 2,748,770 | June 5, 1956 | Moeck |
| 2,768,623 | October 30, 1956 | Marchand |
| 2,881,953 | April 14, 1959 | Kuschel |
| 2,911,972 | November 10, 1959 | Elinger |
| 3,078,847 | February 26, 1963 | Wandell, et al. |
| 3,089,489 | May 14, 1963 | Dunmire |
| 3,187,966 | June 8, 1965 | Klygis |
| 3,261,381 | July 19, 1966 | Roach |
| 3,335,914 | August 15, 1967 | Strazdins, et al. |
| 3,340,869 | September 12, 1967 | Bane |
| 3,419,007 | December 31, 1968 | Love |
| 3,557,788 | January 26, 1971 | Swartz |
| 3,712,295 | January 23, 1973 | Kline |
| 3,736,933 | June 5, 1973 | Szabo |
| 3,938,514 | February 17, 1976 | Boucher |
| 3,977,553 | August 31, 1976 | Cornett, III, et al. |
| 4,018,222 | April 19, 1977 | McAleer, et al. |
| 4,046,145 | September 6, 1977 | Choksi, et al. |
| D 246,321 | November 8, 1977 | Lofman |
| 4,130,117 | December 19, 1978 | Van Eck |
| 4,168,032 | September 18, 1979 | Sneider |
| 4,213,456 | July 22, 1980 | Bottger |
| 4,248,227 | February 3, 1981 | Thomas |
| 4,282,986 | August 11, 1981 | af Ekenstam, et al. |
| 4,357,937 | November 9, 1982 | Burrell, Jr., et al. |
| 4,411,656 | October 25, 1983 | Cornett, III |
| 4,465,472 | August 14, 1984 | Urbaniak |
| 4,502,616 | March 5, 1985 | Meierhoefer |
| 4,506,793 | March 26, 1985 | MacGregor, et al. |
| 4,548,601 | October 22, 1985 | Lary |
| 4,610,670 | September 9, 1986 | Spencer |
| 4,643,309 | February 17, 1987 | Evers |
| 4,753,638 | June 28, 1988 | Peters |
| 4,883,473 | November 28, 1989 | Thomas |
| 4,944,736 | July 31, 1990 | Holtz |
| 4,955,871 | September 11, 1990 | Thomas |
| 4,966,312 | October 30, 1990 | Waring |
| 4,994,039 | February 19, 1991 | Mattson |
| 5,035,689 | July 30, 1991 | Schroeder |
| 5,102,398 | April 7, 1992 | Farris |
| 5,215,221 | June 1, 1993 | Dirksing |
| 5,222,950 | June 29, 1993 | Eisenberg |
| 5,242,422 | September 7, 1993 | Schneberger, et al. |
| 5,334,173 | August 2, 1994 | Armstrong, Jr. |
| 5,356,406 | October 18, 1994 | Schraga |
| 5,370,626 | December 6, 1994 | Farris |
| 5,374,263 | December 20, 1994 | Weiler |
| 5,409,125 | April 25, 1995 | Kimber, et al. |
| 5,478,322 | December 26, 1995 | Farris, et al. |
| 5,509,906 | April 23, 1996 | Poynter |
| 5,538,506 | July 23, 1996 | Farris, et al. |
| 5,716,346 | February 10, 1998 | Farris |

| | FOREIGN PRIOR ART | |
| --- | --- | --- |
| PATENT NO. | ISSUE DATE | INVENTOR |
| FR 470700 | April 7, 1914 | Viviez |
| DE 446819 | July 7, 1927 | Gaertner |
| DE 556491 | August 10, 1932 | Meyer |
| GB 0386298 | February 9, 1933 | Charlier |
| DE 0577611 | June 2, 1933 | Schuckertwerke |
| GB 557400 | November 18, 1943 | Wirth |
| CH 0279468 | March 1, 1952 | Burmester |
| CH 0092396 | October 15, 1959 | Merck & Co., Inc. |
| FR 1316596 | December 26, 1962 | Bouet |
| FR 1330410 | May 13, 1963 | Modiano |
| AU 278032 | December 2, 1965 | Calmic Limited |
| FR 2058585 | May 3, 1971 | Darbon |
| WO 87/01944 | April 9, 1987 | Axipac Limited |
| FR 2594687 | August 28, 1987 | Hosnedl |
| EU 324257 | July 19, 1989 | Smith Industries |
| EU 350772 | January 17, 1990 | Hansen |
| DE 3827335 | February 15, 1990 | Pfeiffer E & Co. |
| SU 1553135 | March 30, 1990 | Popov |

SUMMARY OF THE INVENTION

The instant invention takes into account the fact that not all syringe related deployments require the elaborate methodologies and structure of the prior art in order to be effective. One common scenario involves catheter flushing which occurs predominately in a hospital environment and requires that a flush be applied in the catheter prior to and subsequent to the utilization of the catheter for the delivery of medicine. Flushes typically include HEPARIN or saline in sufficient quantity to purge the catheter line free from the tendency of blood at the site from clotting.

Other examples where it is not essential to deliver extremely precise dosages include intermuscular and some vaccine injections and situations where exigent circumstances (i.e., time is of the essence) and the portability of the medicine far outweighs the risks associated with time delay (e.g., battle field environments).

The instant invention displays a variety of techniques which offer varying degrees of precision by taking an economical medicine storage device expeditiously and immediately deploying it without intervening manipulations.

At its broadest, the instant invention is directed to a device configured as a vial, preformed with the medication contained therewithin which can serve as the dosage administering device immediately. Initially, the liquid within the vial is sequestered from gas, commonly introduced during the manufacturing process. Once this sequestration has occurred, and perhaps sequestering some of the liquid with the gas, the vial can be oriented to push a quantity of the liquid immediately to its intended site. The outlet of the vial can have any of several contours, some of which are standardized by convention. For example, a luer coupling can be disposed at the outlet, a spike can be deployed at the outlet, or an outlet which is complemental to a luer can be found at the outlet end.

Various instrumentalities can be disposed on the exterior in order to act as an external plunger operating on exterior sidewalls of the vial to urge the liquid out from the vial while retaining the gas therewithin. All instrumentalities act on sidewalls of the vial.

OBJECTS OF THE INVENTION

Accordingly, it is a primary object of the present invention to provide a new and improved elastically deformable vial including means to provide external pressure thereto, collapsing the vial to remove the liquid therefrom, thus acting as an external syringe plunger.

A further object of the present invention is to provide a device as characterized above which is economical in construction, aseptic in fact and durable in use.

Viewed from a first vantage point, it is an object of the present invention to provide a dose administering device, comprising, in combination: a closed end wall, a flexible, collapsible sidewall circumscribing the end wall, an outlet coupling at an end of the sidewall opposite the closed end wall, fluid in said device, and plunger means disposed on an exterior of said device's flexible sidewall to eject fluid by constricting the sidewall.

Viewed from a second vantage point, it is an object of the present invention to provide a method for medicinal dosing, the steps including: sequestering gas from liquid in a vial, constricting the vial to sequester the gas in one area, opening the vial at a liquid containing other area and squeezing the liquid from the vial by deforming the vial.

Viewed from a third vantage point, it is an object of the present invention to provide an apparatus for dosing, comprising, in combination: a vial formed from elastically deformable material and having a sealed outlet, liquid contained within the vial, means exterior the vial for distorting an interior of the vial into two zones, one zone with liquid adjacent the outlet, another zone predominately with gas, the exterior means including means for squeezing the liquid from the vial upon unsealing the outlet.

These and other objects will be made manifest when considering the following detailed specification when taken in conjunction with the appended drawing figures.

BRIEF DESCRIPTION OF THE DRAWINGS

FIG. 1 is a perspective view of the apparatus according to one form of the present invention.

FIG. 2 shows the vial associated therewith.

FIG. 3 shows the vial of FIG. 2 deployed on the device of FIG. 1.

FIG. 4 is a schematic depiction of the apparatus of FIG. 3 in use.

FIG. 5 shows a second stage of the apparatus of FIG. 3 in use.

FIG. 19 shows FIGS. 17 and 18 in another stage.

FIG. 20 shows an adjustment capability of the instrument in FIGS. 17 through 19.

FIG. 21 shows an initial manipulative step in using the vial.

FIG. 22 shows a stage in manipulating the vial.

FIG. 23 shows a further stage of FIG. 22.

DESCRIPTION OF PREFERRED EMBODIMENTS

Figure 6:
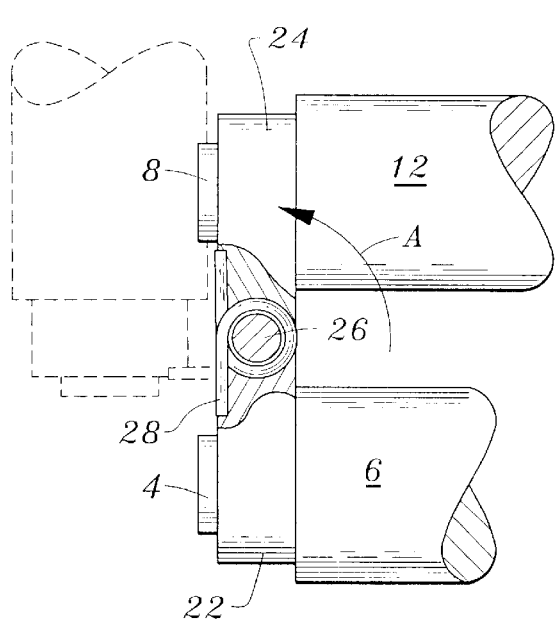
FIG. 6 is a detail of one enabling component of that which is shown in FIG. 1.

Considering the drawings, wherein like reference numerals denote like parts throughout the various drawing figures, reference numeral 10 is directed to the apparatus according to one form of the present invention.

In its essence, the apparatus includes a rectangular hand grip 2 which transversely supports a pair of rollers 6, 12 at one end thereof. The rollers 6, 12 can be oriented to gird a vial 50, and remove the contents therefrom. Initially, the vial 50 is oriented as shown in FIG. 21 so that the gas appears at a tab end 52 of the vial and the liquid L is adjacent an outlet 54. At this stage, note the outlet 54 remains closed with a removable opener 56 integrally formed thereto. Once the gas has been sequestered adjacent the tab 52, the pair of rollers 6 and 12 constrict the vial 50 as shown in FIGS. 3 and 4. This constriction is sufficiently effective to sequester substantially all of the liquid L to the left of FIG. 4 and all of the gas G to the right of the rollers.

Figure 7:
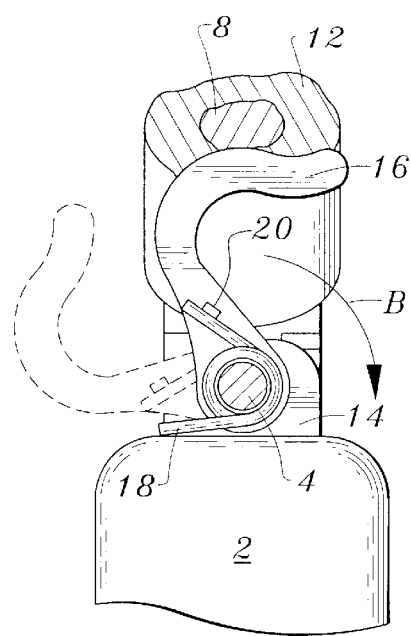
FIG. 7 is another enabling component of that which is shown in FIG. 1.

FIGS. 6 and 7 show details of how the rollers cooperate against the vial to facilitate constriction. The left hand side of FIG. 1 is shown in FIG. 6 and includes upper and lower bearing collars 24, 22 into which roller spindles 8, 4 are placed. The roller spindles allow rotation of the rollers 12, 6 thereon. The upper bearing collar 24 is hinged to the lower bearing collar 22 Reshown in FIG. 1 by means of a pivot hinge 26 which extends between ears 27 reaching up from the lower bearing collar 22. A lower portion of the upper bearing collar 24 is necked-down to nest in between the ears 27. The converse could have also been used for support where the ears are on the upper bearing collar and the necked-down portion on the lower bearing collar. FIG. 6 shows a torsion spring 28 wrapped around the pivot hinge 26 to provide biasing and urge the rollers 6, 12 to naturally go from the open position of FIG. 1 to the closed position of FIG. 4. Thus, work has to be done along arrow "A" to separate the rollers.

Figure 8:
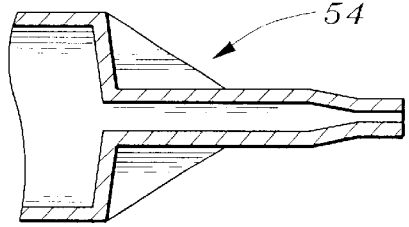
FIG. 8 shows a first possible outlet on the vial.
Figure 9:
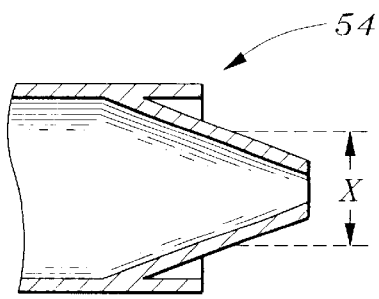
FIG. 9 shows a second alternative outlet on the vial.
Figure 10:
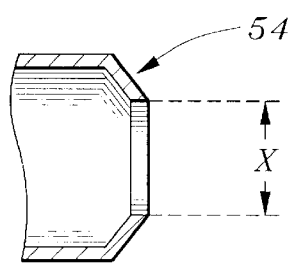
FIG. 10 shows a third alternative outlet on the vial.

FIG. 7 reflects details of the right hand side of the rollers of FIG. 1, and shows a catch mechanism that tightly captures the upper roller to the lower roller. The catch is in the form of a slip hook 16 which when deployed as shown in FIG. 3 overlies the upper roller spindle 8. When the vial 50 is so captured, minimal clearance exists between the opposite walls of the vial as shown in FIG. 4. The rollers 6, 12 themselves may be constructed from any suitable material and may have a durametric value which assures that the opposite walls of the vial are in relatively tight tangential registry. The force B exerted by the hook 16 assures a positive locking between the upper and lower rollers via their respective spindles and is enhanced by a torsion spring 18 wound about the lower spindle 4 and having a free end abutting against the handle 2. An opposite free end includes a pip 20 that locates on a complementally formed indent on the hook 16. The spring 18 ensures positive engagement and urges the hook 16 to the closed and latched position so that force is required opposite arrow "B" to unlatch the hook. FIG. 3 shows the position where the rollers are set on to the vial 50 and the vial opening 54 has been exposed by removing the closure 56. The vial 50 can then be docked onto a fluid receiving device 100 shown to the left of FIG. 4. This device can be a syringe needle if the vial 50 has a luer coupling as shown in FIG. 9 or may be a complementally formed luer receiver as shown in FIG. 10 which as a dimension X, complementally to the taper of the luer in FIG. 9 upstream from its opening to allow frictional engagement thereover. The outlet 54 may also be configured as shown in FIG. 8 which is termed a cannula spike.

Typically, when the vial 50 is used as a flushing device, the need for a precise amount of liquid dispensed by the vial 50 is not as critical as when one is dispensing certain pharmacological substances. Flushing frequently entails the washing of a catheter site with heparin or saline and is not critical with respect to the precise amount used at the catheter site. Where precise dosing is desired, the vial can be filled with a desired volume or gradations 49 disposed on the vial (shown in FIG. 2) may be utilized.

Figure 11:
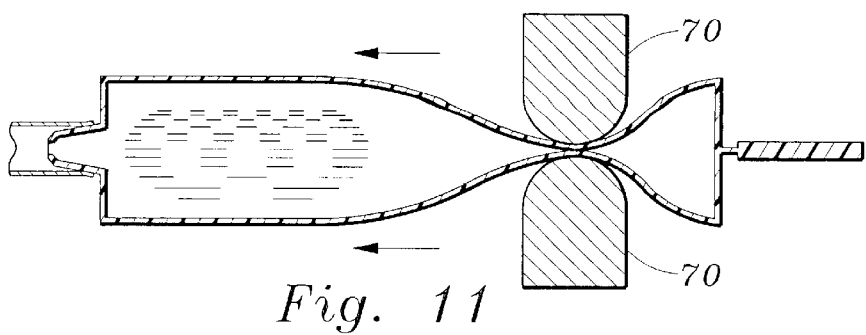
FIG. 11 is an alternative embodiment to FIGS. 1 through 7.
Figure 12:
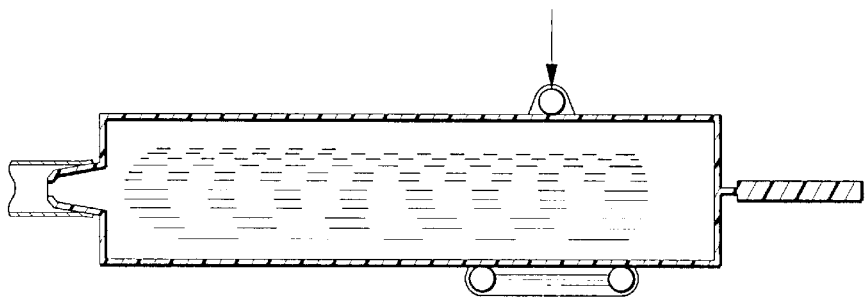
FIG. 12 is another embodiment compared to FIGS. 1 through 7.
Figure 13:
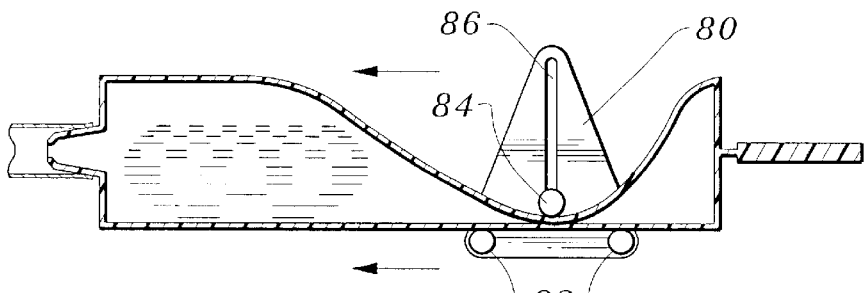
FIG. 13 shows FIG. 12 in a second deployed state.

Various other instrumentalities for causing the liquid to be urged from the vial 50 are shown in FIGS. 11 through 20. In FIG. 11, the rollers are replaced with upper and lower pressure administering devices 70 which do not rotate, but slide from right to left to remove the liquid. The pressure imposed and the coefficient of friction of such an anvil-type device 70 is designed to provide sure, positive motion. Each anvil has a curved smooth bottom surface to encourage point contact where they address one another. The curve also provides low stress on the vial. FIG. 12 shows a variation in which a triangular frame 80 supports tines or two lower rollers 82 and an upper tine or roller 84 constrained to operate within a trackway 86 which is vertically disposed when in the FIG. 13 orientation. Roller 84, when moved from its highest elevation to its lowest elevation through the trackway 86 provides the constriction of the vial and allows the rollers to translate from right to left of that drawing figure.

Figure 14:
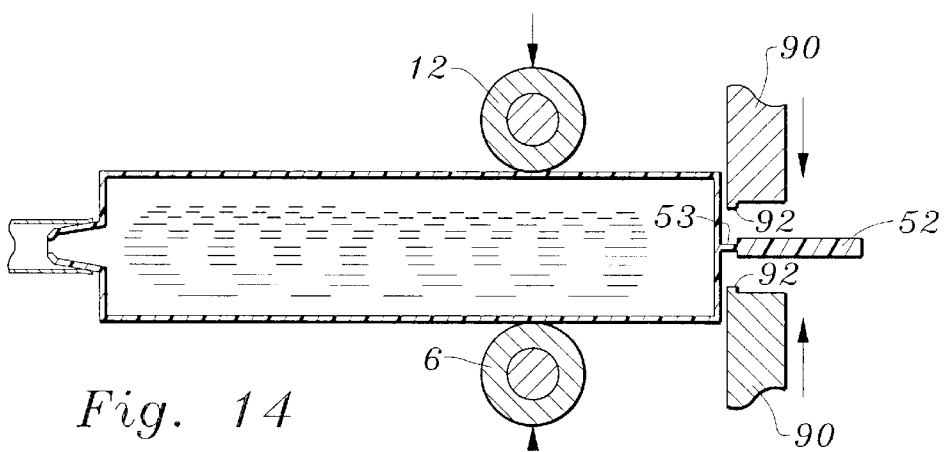
FIG. 14 is another embodiment.
Figure 15:
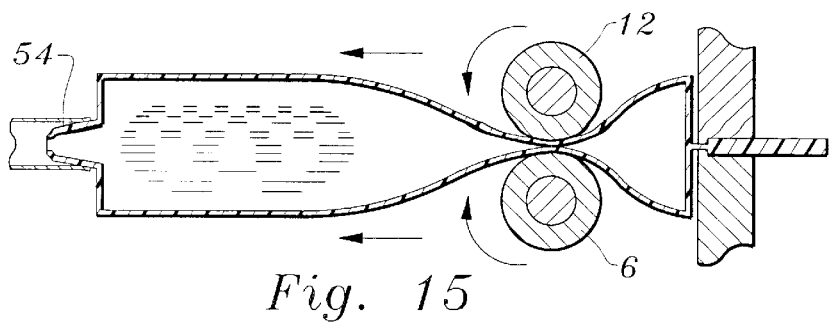
FIG. 15 shows FIG. 14 in a deployed configuration.
Figure 16:
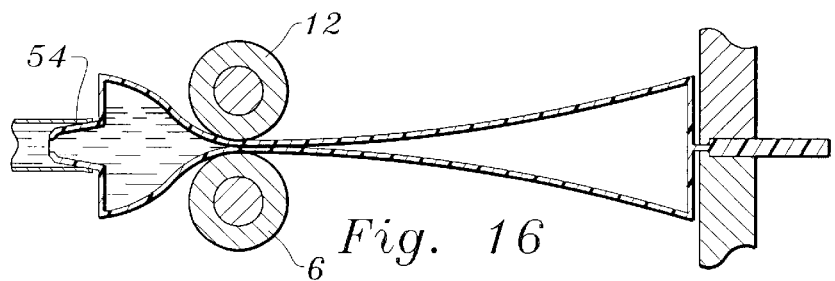
FIG. 16 shows FIGS. 14 and 15 in use.
Figure 17:
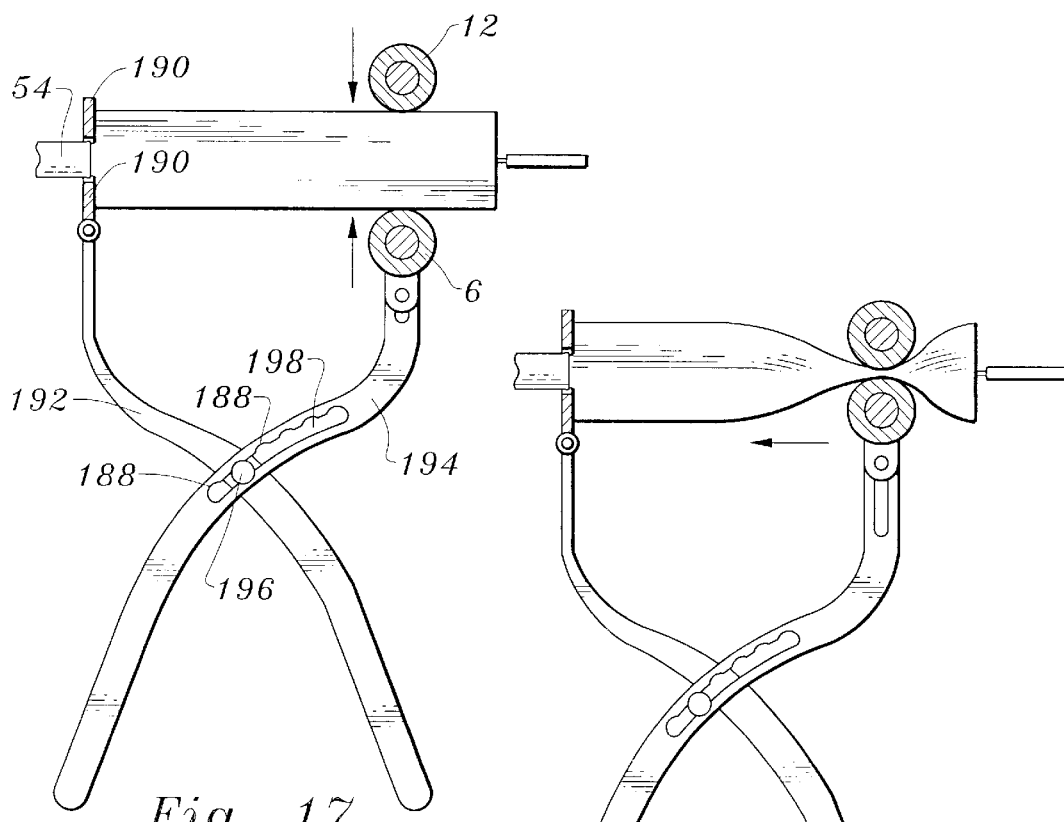
FIG. 17 is a schematic depiction of another variation.
Figure 18:
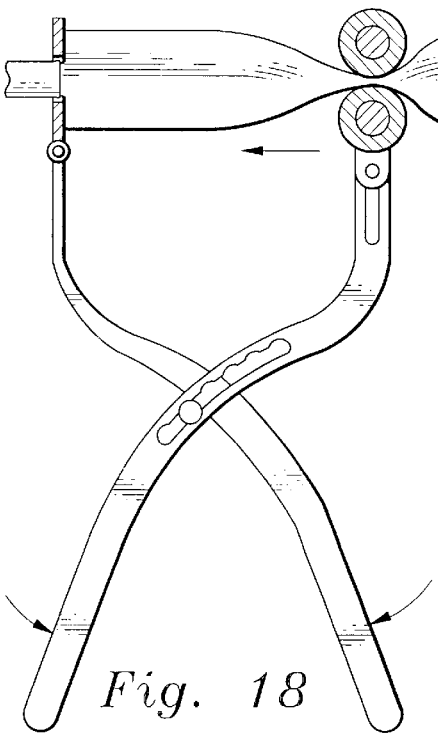
FIG. 18 shows FIG. 17 in the deployed configuration.

FIGS. 14 through 16 show the roller arrangement of FIG. 1, and adds a retaining mechanism 90 located above and below the tab 52. The retaining mechanism 90 replaced the FIG. 4 finger pressure and acts as jaws which allow the tab to remain relatively stationary (compared to the rollers) and therefore the vial when the rollers 6 and 12 are first constricted against the vial and then relatively translated. The retaining mechanism 90 includes teeth 92 which are dimensioned to grip within a narrowed-down waist 53 where the tab 52 affixes to the main body of the vial 50. FIGS. 15 and 16 show the retaining mechanism 90 engaged on the vial with the rollers 6, 12 advancing towards the outlet 54.

FIGS. 17 through 20 show an operation similar to FIGS. 14 through 16 in which the hand tool operates oppositely from that which is shown in FIGS. 14 through 16. In other words, the retaining jaws 90 in FIGS. 14 and 16 are instead modified and located at the outlet end 54 of the vial. These modified retaining devices 190 are fixed to a first link 192 in a pliers-type of arrangement. It should be appreciated that any link mechanism associated with FIGS. 14 through 16 would operate similar to that which is shown in FIGS. 17 through 20. In FIGS. 17 through 20 the rollers are attached to a second link 194 of the mechanism and a pivot 196 extends in between them. The pivot 196 is shown as being located on the first link 192. The second link 194 includes a slot 198 having a plurality of stops 188 depicted as undulations for adjustment of the two links with respect to one another by orientation of the pivot 196 in any of the undulation stops 188 formed in the slot 198. The upper extremities of each of the links may include hinges 201, 203 respectively on the first link 192 and second link 194. These hinges allow articulation as the links move from an open position to a closed position as shown in FIG. 19. In addition, at least one link, preferably the second link 194 constrains its hinge 203 to operate in a trackway 205 to provide further freedom of motion and prevent tool binding.

FIGS. 21 through 23 schematically depict the process of removing liquid from the vial. First sequester the gas into the vial adjacent the tab 52. Then crease the vial below the gas and next remove the cap 56 from the opening. Squeeze out the liquid.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. A dose administering device, comprising, in combination:
   a closed end wall,
   a flexible, collapsible sidewall circumscribing said end wall,
   an outlet coupling at an end of said sidewall opposite said closed end wall, liquid and gas in said device, and plunger means with means to be positioned on an exterior of said device's flexible sidewall at a transition between the gas and the liquid to eject the liquid by constricting said sidewall.

2. The device of claim 1 wherein said plunger means includes means to sequester substantially all liquid in the fluid adjacent said outlet coupling.

3. A dose administering device, comprising, in combination:

a closed end wall, a flexible, collapsible sidewall circumscribing said end wall, an outlet coupling at an end of said sidewall opposite said closed end wall, fluid in said device with liquid adjacent the outlet coupling and gas adjacent said closed end wall, and plunger means with means to be positioned on an exterior of said device's flexible sidewall at a transition between liquid and gas to eject liquid by constricting said sidewall, wherein said outlet coupling is formed as a luer coupling.

4. A dose administering device, comprising, in combination:

a closed end wall, a flexible, collapsible sidewall circumscribing said end wall, an outlet coupling at an end of said sidewall opposite said closed end wall, liquid and gas in said device, and plunger means with means to be positioned on an exterior of said device's flexible sidewall at a transition between the gas and the liquid to eject liquid by constricting said sidewall, wherein said outlet coupling is formed as a spike.

5. A dose administering device, comprising, in combination:

a closed end wall, a flexible, collapsible sidewall circumscribing said end wall, an outlet coupling at an end of said sidewall opposite said closed end wall, liquid and gas in said device, and plunger means with means to be positioned on an exterior of said device's flexible sidewall at a transition between the gas and the liquid to eject liquid by constricting said sidewall, wherein said outlet is configured as a conical taper narrowing from said sidewalls towards an axial centerline to frictionally overlie a luer coupling.

6. A dose administering device, comprising, in combination:

a closed end wall, a flexible, collapsible sidewall circumscribing said end wall, an outlet coupling at an end of said sidewall opposite said closed end wall, liquid and gas in said device, and plunger means with means to be positioned on an exterior of said device's flexible sidewall at a transition between the gas and the liquid to eject liquid by constricting said sidewall, wherein said plunger means is embodied as a plurality of rollers straddling said device, including a tab projecting from said end wall of said device and retaining means located above and below said tab for grasping said tab to facilitate motion of said rollers with respect to said tab.

7. A medicinal dose administering device, comprising, in combination:

a closed end wall, a flexible, collapsible sidewall circumscribing said end wall, an outlet coupling at an end of said sidewall opposite said closed end wall, medicinal liquid in said device along with gas, and plunger means with means to be positioned on an exterior of said device's flexible sidewall at a transition between the gas and the liquid to eject medicinal liquid by constricting said sidewall.

* * * * *